United States Patent [19]

Hale et al.

[11] Patent Number: 5,786,176
[45] Date of Patent: Jul. 28, 1998

[54] RECOMBINANT CDW52 ANTIGEN

[75] Inventors: Geoffrey Hale, Cambridge; Herman Waldmann, Oxford; Masahide Tone, Cambridge; John Tite; Christine Hale, both of Breckenham, all of Great Britain

[73] Assignee: British Technology Group Limited, London, England

[21] Appl. No.: 374,533

[22] PCT Filed: Jul. 14, 1993

[86] PCT No.: PCT/GB93/01482

§ 371 Date: Feb. 3, 1995

§ 102(e) Date: Feb. 3, 1995

[87] PCT Pub. No.: WO94/02604

PCT Pub. Date: Feb. 3, 1994

[30] Foreign Application Priority Data

Jul. 15, 1992 [GB] United Kingdom .................... 9215071

[51] Int. Cl.$^6$ .................................................. C12N 15/09
[52] U.S. Cl. .................... 435/69.3; 435/172.3; 435/352; 435/362
[58] Field of Search .............................. 435/7.21, 7.24, 435/7.95, 69.3, 172.3, 240.2, 325, 352, 362, 243; 530/326, 327

[56] References Cited

U.S. PATENT DOCUMENTS 5,354,665  10/1994  Wallner et al. .......................... 530/395
5,494,999   2/1996  Hale et al. .............................. 530/326

FOREIGN PATENT DOCUMENTS 9218530  10/1992  WIPO .

OTHER PUBLICATIONS

M-Q Xia et al, European Journal of Immunology, 21, 1677–1684, 1991.
G. Mave et al, Tissue Antigens, 35, 118–127, 1990.
L. Riechmann et al, Nature, 332, 323–327, 1988.
A.R. Carroll et al, Molecular Immunology, 29, 821–827, 1992.

*Primary Examiner*—David Saunders
*Attorney, Agent, or Firm*—Nixon & Vanderhye P.C.

[57] ABSTRACT

The invention relates to recombinant cell lines, in particular mamalian cell lines, capable of expressing recombinant CDw52 antigen or an antigenic fragment thereof. The cell lines can be used for the production of recombinant CDw52 antigen and in assaying for anti-CDw52 antibody in a sample.

6 Claims, No Drawings

RECOMBINANT CDW52 ANTIGEN

This invention relates to a recombinant CDw52 antigen which may be used in assaying for, purifying or inducing anti-CDw52 antibodies.

The CAMPATH-1 family of monoclonal antibodies recognise an antigen expressed on the majority of human lymphocytes and monocytes (CAMPATH is a Registered Trade Mark of The Wellcome Foundation Limited). At the Fourth Leucocyte Workshop these antibodies were given the provisional designation CDw52. The CDw52 antigen is an unusually good target for complement-mediated attack and for this reason the IgM antibody, CAMPATH-1M, has been widely used for removal of T lymphocytes from donor bone marrow to prevent graft-versus-host disease.

The CDw52 antigen is expressed in most cases of lymphoid malignancy and serotherapy of lymphoma and leukaemia with CAMPATH-1 antibodies has therefore been attempted. The rat IgG2b, CAMPATH-1G, which activates both complement and cell-mediated killing, has been found to be rather effective in this context. Recently, a human IgG1 antibody (CAMPATH-1H) with the same specificity has been constructed by recombinant DNA technology and this can be administered for a longer period and produces even better clinical results (see Riechmann et al., Nature, 332, 323–327, (1988) and Hale et al., The Lancet, 2, 1394–1399 (1988)). Campath-1H has proved to be effective for lymphocyte depletion in vivo and is being tested for the treatment of lymphoma, transplant rejection and various autoimmune diseases.

It is apparent that not all differentiation or tumour associated antigens are equally good targets for serotherapy and the reasons why the CAMPATH-1 antigen is so good are not yet clear. Its abundant expression (about $5 \times 10^5$ molecules per lymphocyte) and lack of modulation are probably relevant factors but do not provide a complete explanation since even small (sub-saturating) amounts of antibody are effective compared with other specificities.

Hale et al., (Tissue Antigens, 35, 118 (1990)) reported that about 50% of the CAMPATH-1 antigen could be removed from peripheral blood lymphocytes by treatment with glycosylphosphatidylinositol (GPI)-specific phospholipase C (from *B. thuringiensis*). This shows that at least some of the antigen is anchored by GPI and possibly all of it since a similar partial resistance has been observed with other GPI-linked antigens.

Hale et al., also reported that the CAMPATH-1 antigen can be extracted from cell homogenates into the aqueous phase of a chloroform:methanol:water system and it can be detected by Western blotting as a broad band of apparent molecular weight 21–28 kD. Treatment with N-glycanase reduces the apparent molecular weight to about 6 kD but the antigenicity is not diminished. The molecule is resistant to treatment with narrow specificity proteases but treatment with broad specificity proteases reduces its apparent molecular weight substantially without destroying antigenicity. However, the antigen is very sensitive to treatment with mild alkali.

Xia et al., (Eur. J. Immunol. 21, 1677–1684 (1991)) purified the CAMPATH-1 (CDw52) antigen from human spleen and found the antigenic epitope to be heat stable but sensitive to mild alkali treatment. Experiments with phosphatidylinositol-specific phospholipase C also indicated that it is anchored by a GPI anchor. An N-terminal sequence of 11 amino acids was determined, followed by an abrupt stop. Using short overlapping mixed oligonucleotide primers, cDNA synthesized from the mRNA of a human B cell line was amplified by the polymerase chain reaction. The product was used to isolate CDNA clones and the full amino acid sequence of the CAMPATH-1 antigen was deduced.

The amino acid sequence was found to consist of 37 amino acid residues plus a 24-residue signal peptide. It has all the features expected for a GPI-anchored membrane protein except that the predicted mature protein is remarkably short, comprising no more than 18 residues and possibly as few as 12 (depending on the GPI linkage site). Potential attachment sites for carbohydrate are present and it is shown that the antigen contains N-linked oligosaccharide (s). This structure accounted for the known properties of the antigen, though the exact reasons why it is such a good target for cell lysis in vitro and in vivo remain unclear.

In connection with the work of Xia et al., described above, reference should also be made to International Application PCT/GB92/00705 (WO92/18530).

It has now been found that the Campath-1 (CDw52) antigen can be expressed in recombinant cell lines in a form which is recognised by anti-CDw52 antibodies. This result is surprising and by no means predictable based on the known properties of the CDw52 antigen. Thus it was known that the antigen is highly glycosylated and that the epitope recognised by anti-CDw52 antibodies such as Campath-1H is sensitive to mild alkali but resistant to proteolytic enzymes. This suggested that the epitope was not simply composed of a linear or conformational arrangement of amino acids. Accordingly, it was unpredictable that host cells and particularly non-human host cells would be capable of correctly processing and glycosylating the CDw52 (Campath 1) antigen to provide a fully functional recombinant antigen recognised by anti-CDw52 (Campath 1) antibodies such as Campath-1H.

The present invention provides a recombinant cell line capable of expressing recombinant CDw52 (Campath 1) antigen or a fragment thereof in a functional form capable of being recognised by antibodies raised against the natural CDw52 antigen.

Cell lines according to the invention will generally contain DNA encoding the CDw52 antigen or an antigenic fragment thereof, in a form capable of expression. The DNA may be genomic DNA or preferably cDNA or synthetic DNA and will be under control of a promoter and other regulatory elements suitable for the host cell line.

The present invention also provides recombinant CDw52 antigen or an antigenic fragment thereof in a functional form capable of being recognised by antibodies raised against the natural CDw52 antigen. By virtue of having been produced in a recombinant cell line, the recombinant CDw52 antigen will be characterised by the absence of impurities with which natural purified CDw52 antigen, for example CDw52 antigen purified from human spleen cells, is normally associated. The recombinant CDw52 antigen will also be characterised by glycosylation associated with the type of host cells in which it has been produced. Thus, recombinant CDw52 antigen produced in Chinese Hamster Ovary (CHO) cells will have CHO glycosylation and recombinant CDw52 antigen produced in Baby Hamster Kidney (BHK) cells will have BHK glycosylation.

As used herein, the term "antigenic fragment" of the CDw52 antigen means a fragment capable of acting as an antigen in an antigen-antibody binding reaction with antibodies raised against the natural CDw52 antigen. Antigenic fragments will generally be at least 2 to 6 amino acid residues long, for example 2, 3, 4, 5, 6 or more residues long.

Genomic or cDNA encoding the CDw52 antigen may be produced by conventional methods of recombinant DNA technology. As noted above the isolation of cDNA clones encoding the CDw52 (Campath 1) antigen is described by Xia et al., Eur. J. Immunol., 21, 1677-1684 (1991) and this paper also discloses the full DNA and deduced amino acid sequences of the antigen. cDNA encoding the CDw52 antigen can be used as a probe to isolate genomic DNA encoding the same antigen from a genomic DNA library again using standard techniques. Alternatively, DNA encoding the CDw52 antigen can be synthesised by standard techniques of DNA synthesis based on the known DNA and amino acid sequences.

The DNA encoding the CDw52 antigen can be incorporated into an expression vector, again using the standard techniques of recombinant DNA technology and the expression vector used to transform a suitable host cell line. Construction of expression vectors and other standard techniques of recombinant DNA technology may be carried out for example in accordance with the procedures described in Molecular Cloning: A Laboratory Manual, Second Edition, Sambrook et al., Cold Spring Harbor Laboratory.

The host cell must be capable of expressing the recombinant antigen in a functional form and therefore, should be a eukaryotic cell such as a mammalian cell e.g. myeloma or Chinese Hamster ovary (CHO), Baby Hamster Kidney (BHK) or JURKAT cells which are capable of carrying out post-translational modifications, in particular, correct folding and glycosylation. Such cells can be cultured in vitro quite successfully and express functional antigen. Yeast or insect cells may also serve as host cells as they can also carry out desired post-translational modifications. cDNA encoding the CDw52 antigen can be transfected in a vector also containing a selectable marker. The selectable marker may or may not be of a dominant nature. Examples of selectable markers include adenosine deaminase (Kaufman et al., Proc. Natl. Acad. Sci. USA, 83, 3136–40 (1989)) asparagine synthetase (Cartier et al., Mol. Cell Biol., 7, 1623–28 (1987)), E. coli trpB gene and Salmonella hisD gene (Hartman et al., Proc. Natl. Acad. Sci. USA, 85, 8407–51 (1988)), M2 mouse ribonucleotide reductase (Thelander et al., EMBO J, 8, 2475–79 (1989)), human multidrug resistance gene (Kane et al., Gene, 84, 439–446 (1989)), glutamine synthetase (Bebbington et al., DNA Cloning Vol III, Ed. D. M. Glover, 163–188, IRL Press (1987)), xanthine gluanine phosphoribosyl transferase (gpt) (Mulligen et al., Science, 209, 1422–27 (1980)), hygromycin B (Santerre et al., Gene, 30, 147–156 (1984)), neomycin gene (Southern et al., J. Mol. Appl. Genet., 1, 327–341 (1982)), and dihydrofolate reductase (dhfr) (Subramani et al., Mol. Cell Biol., 1, 854–868 (1981)).

A preferred selectable marker is dhfr which is usually employed with a parental CHO cell line of the dhfr⁻ phenotype (Urlaub et al., Proc. Natl. Acad. Sci. USA, 77, 4216–4220 (1980)). Successfully transfected CHO cells with possess the dhfr⁺ phenotype and can be readily selected by culturing the colonies on media devoid of thymidine and hypoxanthine and optionally containing methotrexate (MTX). A further preferred selectable marker is a dominant resistance marker, such as neomycin (neo). CHO cells successfully transfected with this marker can be readily selected by culturing the colonies in media containing the antibiotic Geneticin, as analogue of neomycin.

Particularly preferred for use in myeloma or CHO cells is the glutamine synthetase or GS system which is described in WO 87/04462. Cells which have been successfully transfected with this marker can be selected by culturing colonies in media containing certain levels of methionine sulphoximine (Msx).

A selectable marker may also provide the basis upon which the DNA encoding the CDw52 antigen may be amplified. In transfection of a cell line, the vector DNAs are often integrated into the chromosome of the cell at the same locus. Thus, the use of a selectable marker as the basis for amplification normally results in a parallel increase in the copy number of both the DNA encoding both the selectable marker and the DNA of interest. One selectable marker for use in this way is dhfr which enables the desired amplification selection through the use of increasing concentrations of MTX. Also preferred is the GS marker which can be used to enable amplification selection by employing increasing concentration of Msx.

The selectable markers are of course under the control of regulatory elements of DNA so as to provide for their expression. The regulatory elements are preferably of a viral source, such as from DNA tumour viruses. Particularly preferred are the use of an SV40 or adenovirus major late promoter. It is particularly advantageous in this regard to remove the enhancer element from the promoter thus effectively "crippling" it. This modification allows for greater levels of gene amplification at each concentration of methotrexate selection than would otherwise occur if a strong promoter was used. In the case of the use of GS as a selectable marker, an example of a suitable promoter is the mouse metallothionein promoter or preferably the human cytomegalovirus (hCMV)-MIE promoter described in WO89/01036.

The DNA encoding the CDW52 antigen is also under the control of regulatory elements of DNA so as to provide for its expression. The regulatory elements may be of viral origin and examples include those mentioned above in conjunction with the expression of dhfr or GS as a selectable marker. Another example is the use of the β-actin promoter and cognate β-actin polyadenylation signal.

The vector may also contain an SV40 origin of replication to allow for the vector constructs to be checked by rapid transient assay for example in COS cells.

Transfection of the cell line with the expression vector may be carried out by using standard transfection procedures, such as calcium phosphate precipitation or lipofectin. Selection of the desired transfected cell line may be carried out in accordance with standard procedures known for the particular selectable markers.

Culture of the cell line may be carried out in serum-containing or preferably serum-free media. Where the cell line is a CHO dhfr⁻ transformant, the medium preferably lacks hypoxanthine and thymidine and optionally contains MTX.

The present invention also provides a method for the production of recombinant CDw52 antigen or an antigenic fragment thereof which comprises the steps of:

i) providing a suitable host cell line capable of processing CDw52 antigen or an antigenic fragment thereof into a functional form and transformed with DNA encoding the CDw52 antigen or an antigenic fragment thereof, in a form capable of expression;

ii) growing the cell line in a manner such that the CDw52 antigen or an antigenic fragment thereof is expressed in a functional form; and iii) recovering the CDw52 antigen or an antigenic fragment thereof.

The recombinant CDw52 antigen or an antigenic fragment thereof can be recovered and purified using standard techniques of protein purification, for example, methods analogous to those described by Xia et al., Eur. J. Immunol., 21, 1677–1684 (1991) for the recovery of natural CDw52 antigen from human spleen.

The recombinant CDw52 antigen according to the invention may be used to develop simple and reliable assays for the concentration of antibodies recognising this antigen. As noted above antibodies against the CDw52 antigen, such as the humanised antibody Campath 1H, are being developed for use in a number of therapeutic applications. Accordingly, assays for such antibodies will be needed in a number of situations including quality control tests during the production of the antibody and the measurement of serum levels of the antibody during therapy.

Assays in which the purified antigen is used to measure the concentration of antibodies to that antigen are well known and these known types of assay can also be applied to the development of assays for anti-CDw52 antibodies.

According to a further aspect, the present invention provides a method of assaying an anti-CDw52 antibody in a sample, which method comprises contacting the sample with recombinant CDw52 antigen or an antigenic fragment thereof and determining binding of the antibody to the recombinant antigen or the fragment thereof.

The method can be used to detect the presence of anti-CDw52 antibody in the sample in which case it is necessary only to determine whether or not an immunoglobulin has bound to the recombinant antigen. Alternatively, the method may be a semi-quantitative or qualitative assay for the amount of anti-CDw52 antibody in the sample in which case it is necessary to measure the amount of immunoglobulin binding to the recombinant antigen under controlled conditions.

The sample may be, for example, a serum sample or a sample arising during production of an anti-CDW52 antibody such as Campath 1H. The recombinant CDw52 antigen may be immobilised on a solid support such as plastic microtitre plates or plastic beads. Binding of anti-CDw52 antibody to the recombinant CDw52 antigen may be determined in any suitable manner, such as by means of a labelled antiglobulin. The label may be, for example, an enzyme label in which case a substrate for the enzyme also needs to be included. The assay may be carried out as a simultaneous or sequential assay.

As an alternative to the use of purified recombinant CDw52 antigen, it may also be possible to use cells expressing the recombinant antigen, directly in an assay. Thus, cells expressing the recombinant antigen, in particular cells of a clone selected for a high level of antigen expression, can be incubated with the test sample and anti-CDw52 antibody bound to the cells determined (quantitatively or qualitatively) in the manner mentioned above, for example using a labelled antiglobulin. Such a method is particularly suited to the routine analysis of anti-CDw52 antibodies for quality control during production or for monitoring antibody levels during therapy.

The present invention also relates to a test kit suitable for use in an assay for an anti-CDw52 antibody in a sample. In general, the kit comprises:

a) recombinant CDw52 antigen; and b) means for the quantitative or qualitative determination of binding of an immunoglobulin to the antigen following contact of the antigen with the sample.

The recombinant CDw52 antigen according to the invention can also be used in the purification of an anti-CDw52 antibody by affinity chromatography. Accordingly, in another aspect, the present invention provides a process for the purification of an anti-CDw52 antibody which process comprises passing a crude preparation of the antibody over a solid support carrying recombinant CDw52 antigen or an antigenic fragment thereof, and eluting anti-CDw52 antibody bound to the support.

The recombinant antigen may be used in the purification of any antibody recognising the CDw52 (Campath 1) antigen, for example the humanised antibody Campath 1H. The recombinant antigen may be coupled to a solid support and a crude preparation of the antibody passed over it. Only the antibody recognising the CDw52 antigen should bind and the antibody can then be eluted by a change in conditions, for example a pH shift. Suitable crude antibody preparations include medium resulting from the growth of a recombinant cell line, for example a mammalian cell line, producing the antibody in question.

It has recently been found that the CDw52 antigen is expressed on human sperm and is also found in human seminal plasma and a number of anti-CDw52 antibodies have been shown to be capable of immobilising washed human sperm in the presence of complement. There is considerable interest in sperm glycoproteins as possible targets for immune recognition by infertile men or women and the possibility also exists that sperm glycoproteins could form the basis of a contraceptive vaccine for administration either to men or women. In both cases these possibilities would be enhanced if the sperm glycoprotein has some particular sperm-specific modification, e.g. glycosylation. The recombinant CDw52 antigen according to the present invention may thus be a candidate for use in the development of treatments for infertility in men or women associated with immune recognition of the CDw52 antigen in human sperm. The recombinant CDw52 antigen according to the invention may also be a candidate for the development of a contraceptive vaccine for administration to either men or woman.

The recombinant anti-CDw52 antigen can also be used for the selection of variants of anti-CDw52 (Campath 1) antibodies with higher affinity for the antigen. Two complementary types of approach are envisaged and either can be realised using any number of different systems for creating large numbers of genetic variants and expressing them. First the assay method referred to above may be used with fragments of the antigen of low affinity, under conditions where a parental antibody gives marginal binding, to identify mutants of the parental antibody with superior binding ability. Second an affinity column in which the recombinant CDw52 antigen is bound to a solid support could be used to directly select cells or micro-organisms expressing antibody mutants of higher affinity.

The recombinant CDw52 antigen can also be used to generate new monoclonal or polyclonal anti-CDw52 antibodies. According to a further aspect of the present invention, there is provided a process for the preparation of an anti-CDw52 antibody, which process comprises immunising a mammal with recombinant CDw52 antigen or an antigenic fragment thereof.

An immortalized cell line which produces a monoclonal anti-CDw52 antibody may be prepared by a process which comprises immunising a mammal with recombinant CDw52 antigen or an antigenic fragment thereof; fusing cells of lymphoid origin from the immunised mammal with cells of an immortalising cell line; and selecting thus-immortalised cells which produce anti-CDw52 antibody. The selected immortalised cell line which produces anti-CDw52 antibody is then grown to obtain monoclonal CDw52 antibody.

The recombinant CDw52 antigen or antigenic fragment thereof may be administered to the mammal as a conjugate in which the recombinant antigen or fragment thereof is coupled, for example via a side chain of one of the amino acid residues, to a suitable carrier. The carrier molecule is typically a physiologically acceptable carrier. Such conjugates also form part of the invention.

Conventional ways may be used to produce antisera or monoclonal antibody (Kohler and Milstein, Nature, 256, 495–497, (1975)). Hybridoma cells producing monoclonal antibody may be prepared by fusing spleen cells from an immunised animal with a tumour cell. The mammal which is immunised may be a rat or mouse. The hybridomas may be grown in culture or injected intraperitoneally for formation of ascites fluid or into the blood stream of an allogenic host or immunocompromised host. Human antibody may be prepared by in vitro immunisation of human lymphocytes with respect to the peptide or a fragment thereof, followed by transformation of the lymphocytes with Epstein-Barr virus.

Antibody may then be isolated. A pharmaceutical composition may be formulated which comprises a pharmaceutically acceptable carrier or diluent and, as active ingredient, anti-CDw52 antibody prepared according to the invention.

Antibody variants, for example having a high affinity, may be prepared using techniques described in Proc. Natl. Acad. Sci. USA, 86, 5728–5732 (1989) and Science, 246, 1275–1281, (1989). MRNA is isolated from a B cell population, for example spleen or lymph node, from a mammal which produces anti-CDw52 antibody. The mammal may be a rat, mouse or human. Heavy and light chain immunoglobulin CDNA expression libraries are created in bacteriophage lambda vectors. The libraries are screened separately or cross-screened for dual expression of heavy and light chains. After infection of a host such as *E. coli*, lambda or excised plasmid libraries are screened for antibody molecules specific for CDw52.

The invention is illustrated by the following examples.

EXAMPLE 1

BHK Cell Line Expressing CDw52 Antigen cDNA encoding the CDw52 (Campath 1) antigen was obtained by standard techniques from mRNA extracted from the human B-cell line Wein 133 Nacheva et al., Cancer Genetics & Cytogenetics, 28, 145 (1987) and incorporated into plasmid pCAM2 by the method described by Xia et al., Eur. J. Immunol., 21, 1677–1684 (1991) and in WO92/18530 (PCT/GB 92/00705). A CDw52 antigen expression plasmid was constructed based on the plasmid pHBAPr-1-neo (Gunning et al., Proc. Natl. Acad. Sci. USA, 84, 4831–4835 (1987)) which contains the human B-actin promoter. A SalI site (8 bp upstream of the first ATG) and a BamHI site (21 bp downstream from the stop codon) were introduced into the CDw52 cDNA using PCR. The CDw52 cDNA was then excised as a SalI-BamHI fragment and introduced into the SalI-BamHI cloning sites of pHBAPr-1-neo (downstream of the human β-actin promoter) to produce the expression plasmid pHβCAM2.

The expression plasmid pHBCAM2 was then used to transfect a Baby Hamster Kidney cell line (BHK21C13-2P available from European Collection of Animal Cell Cultures, PHLS Centre for Applied Microbiology & Research, Porton Down, Salisbury, U.K. under reference number ECACC 84111301; BHK21C13-2P is a sub-clone of BHK21 described by MacPherson & Stoker, Virology, 16, 147–151 (1962)). $5 \times 10^6$ BHK21C13-2P cells were transfected with 10 µg of pHBCAM2 using Lipofectin (BRL). Stable transfectants were selected by G418 and cloned by the agarose cloning method. One of the cloned transfectants BHK-CAM-G1 was demonstrated to express CDw52 antigen by indirect immunofluorescence staining with a Campath-1G antibody (rat monoclonal IgG2b) or an isotype control antibody (YTH53.1—a human CD59 antibody) and using FITC-conjugated anti-rat Ig for detection. The indirect immunofluorescence staining demonstrated cell surface expression of CDw52 (Campath 1) antigen on the transfected cells but not on parent BHK21C13-2P cells.

The expressed antigen was also detected by immunoblotting. Cell extracts were prepared from BHK21C13-2P, BHK-CAM-G1 and the human B cell line referred to above as the source of mRNA for cloning the Campath-1 antigen cDNA. In each case, $2 \times 10^7$ cells were harvested and resuspended in 100 µl of water. 370 µl methanol and 180 µl chloroform were then added and after rotating for 30 min the mixture was centrifuged and supernatant was transferred to a fresh tube. 120 µl water was added and mixed for 10 min. The mixture was centrifuged and the upper phase was transferred to a fresh tube. After evaporation, the pellets were dissolved in 1×SDS sample buffer (50 mM Tris-HCl (pH 6.8), 100 mM dithiothreitol, 2% SDS-0.1% Bromophenol blue, 10% glycerol) and boiled for 5 minutes. The samples were electrophoresed on a 15% SDS polyacrylamide gel. After transfer to nitrocellulose, the protein filter was incubated with a Campath-1 antibody (Campath-IG) at 4° C. overnight. Antibody binding to protein was detected by peroxidase conjugated anti-rat-IGG and an ESC detection system (Amersham).

27–50kDa broad bands in BHK-CAM-G1 and 21–50 kDa bands in the human B cells were detected. The 21–27kDA molecules in the human B cells may be produced by human specific post-translational modification. High molecular weight molecules observed in BHK-CAM-G1 and the human B cells were broadly distributed over more than 60 kDa on 8% PAGE.

The CDw52 (Campath 1) antigen on human cells is attached to the membrane via a GPI anchor. To investigate whether the antigen expressed on transfectants was also attached via a GPI anchor, transfected BHK21C-2P cells were treated with PI-PLC which cleaves glycolipid anchors. Thus, $1 \times 10^6$ BHK21C13-2P or transfectant BHK-CAM-G1 cells were incubated for 90 minutes at 37° C. in 150 µl of PBS with 0.1µ/ml of *B. thuringingensis* PI-PLC and protease inhibitors (50 µg/ml PMSF, 5 µg/ml peptain, 5 µg/ml leupeptin, 5 µg/ml antipain). The cells were harvested and analysed by indirect immunofluorescence staining using Campath-1G antibody and flow cytometry using FITC-conjugated anti-rat Ig. The PI-PLC treatment significantly removed cell surface CDw52 (Campath 1) antigen from the transfectant BHK-CAM-G1 cells.

The conditions for PI-PLC treatment were checked using Jurkat cells which were treated with PI-PLC under the same conditions and stained with CD59, CDw52 (GPI-anchored antigens) and CD45R (non-GPI anchored antigen) antibodies. Removal of CD59 and CDw52 from the cell surface was observed, but CD45R remained constant under these conditions. This shows that the release of the CDw52 antigen from transfected cells is due to cleavage of the glycolipid anchor and is not due to protease contamination.

EXAMPLE 2

CHO Cell Line Expressing CDw52 Antigen cDNA encoding the CDw52 antigen and obtained from mRNA extracted from K422 cells as described in Example 1 was used as template for PCR amplification. The primers were based on the CDw52 antigen DNA sequence (Xia et al., Eur. J. Immunol., 21, 1677–1684 (1991)) and corresponded to the 5'-untranslated region (bases 23–43) and the 3' region (bases 201–220). The primers were also designed to incorporate a HindIII site at the 5'-end and an EcoRI site at the 3'-terminus. PCR amplification using a standard protocol (Perkin Elmer Cetus kit with modified forward and reverse primers and using 5% DMSO) resulted in the expected band of 206 bp containing the CDw52 coding sequence plus start and stop signals. DNA from this band was isolated from a 3% GTG:1% agarose gel and purified.

The isolated HindIII-EcoRI fragment resulting from PCR was cloned into the commercial vectors PUC18 and PUC19 for sequencing by the dideoxy chain termination method using a Sequenase kit (USB). Several individual colonies were shown to have DNA inserts of the expected sequence and these were cloned further into the expression vector pRDN1. This vector uses the β-actin promoter and polyadenylation tail to control expression of the DNA of interest. The vector also includes a dhfr cassette under regulation of the SV40 promoter and polyadenylation tail to allow for drug (methotrexate) selection of transfected cells.

The mammalian expression vector pRDN-1 is essentially the same as the plasmid pLD9 described by Page et al., to express the Campath-1H antibody light chain (Bio/Technology, 9, 64–68, (1991)) without the light chain cDNA, but with unique EcoRI and HindIII cloning sites.

Plasmid pRDN-1 was constructed as follows:

1. The dhfr selection plasmid p104 (Page et al., supra), contains two HindIII sites which were removed by digesting the plasmid with HindIII, filling in the overhanging ends with the Klenow fragment of E. coli DNA polymerase, blunt-end religation and transformation into E. coli. Miniprep analysis of colonies was performed to identify the correct construct (p104(-H3)) where both HindIII sites were lost and the dhfr gene was orientated downstream of the crippled SV40 promoter.

2. The construct p104(-H3) contains one EcoRI site which was removed by digesting the plasmid with EcoRI, filling in the overhanging ends with the Klenow fragment of E. coli DNA polymerase, blunt-end religation and transformation into E. coli. Miniprep analysis of colonies was performed to identify the correct construct (p104(-H3,-RI)) where the EcoRI site was lost.

3. The construct p104(-H3,-RI) was digested with BamHI, treated with phosphatase. This was then combined as described by Page et al., (supra) in a three way ligation to a BglII to HindIII fragment of the human β-actin promoter (including the 5' untraslated region and the first intron) and a HindIII to BamHI fragment containing the human β-actin 3' untranslated region, polyadenylation signal and 3' flanking sequences. Ligated DNA was transformed into E. coli and miniprep analysis of colonies was performed to identify the correct construct pRDN-1 which contained the complete β-actin expression cassette, and where the direction of transcription of the β-actin promoter would be in the same direction as that of the crippled SV40 promoter.

Cloning the DNA inserts referred to above into pRDN1 gave the final expression construct pRDNAG35 which was first transfected into COS-1 cells (ECACC, Porton Down, Salisbury, U.K.) using Transfectam (Promega) to test for transient expression. FACS analysis of the transfected cells 3 days after expression indicated that about 14% of the cells were staining specifically with FITC-Camnath 1H indicating expression of the CDw52 antigen.

The expression vector pRDNAG35 was then transfected into CHO dhfr⁻ cells (Urlaub et al., Proc. Natl. Acad. Sci. USA, 77, 4216–4220 (1880)) using Transfectam. The transfected cells were initially cultured in selective medium containing methotrexate and FACS analysis of this population revealed low but significant expression of CDw52 antigen.

Cells containing the pRDNAG35 construct were then selected for drug resistance by increasing the levels of methotrexate added to the culture medium. The level of drug was increased sequentially to $3\times10^{-8}$M, $1\times10^{-7}$M and $1\times10^{-6}$M methotrexate. The cell populations generated by these selections were subjected to FACS analysis and found to have increased CDw52 antigen expression roughly as expected, i.e. those resistant to the highest concentrations of methotrexate had the highest level of expression.

An alternative procedure which is equally effective is to culture the transfected cells initially in selective medium which does not contain methotrexate and to add methotrexate only at the stage of selecting cells containing the pRDNAG35 construct.

The $3\times10^{-8}$M and the $1\times10^{-6}$M populations were cloned by limiting dilution and the clones again analysed. Representative clones were selected which expressed medium ($3\times10^{-8}$M clones) or high ($1\times10^{-6}$M clones) levels of CDw52 antigen. These cell line were found to be suitable for the development of an assay in that they are strongly adherent and do not need to be stuck onto assay plates before fixation.

EXAMPLE 3

JURKAT Cell Line Expressing CDw52 Antigen

JURKAT-J6 (ECACC, Porton Down, Salisbury U.K.) is a human T cell line which normally expresses negligible levels of CDw52 antigen. Using the same general method as described in Example 2, JURKAT-J6 cells were co-transfected with the CDw52 expression plasmid pRDNAG35 (see Example 2) and with p321neo (Wan Kim et al., Gene, 91, 217–223 (1990)). Since JURKAT-J6 cells are dhfr⁺, co-transfection with p321neo was required to provide a selectable marker (neomycin resistance). Transfected cells were selected in G418 and cloned by limiting dilution to provide various cloned cell lines expressing CDw52 antigen at different levels.

EXAMPLE 4

Measurement of Serum Levels of CDw52 Antibodies (i) Rationale

Samples of test sera from patients treated with anti-CDw52 antibodies are incubated with the antigen-positive transfectants. Control samples of normal human serum to which known amounts of anti-CDw52 antibody have been added are incubated under identical conditions. Precautions are taken to avoid complement-mediated lysis of the target cells. The cells are thoroughly washed to remove excess serum and then incubated with a suitable detection reagent, eg FITC-labelled anti-IgG. Finally the cells are washed and the fluorescence is measured (or the detection reagent is otherwise developed). A standard curve is constructed from the standards and the amount of anti-CDw52 antibody in the test samples is calculated by interpolation from this curve. An example illustrating the methodology is given below.

(ii) Materials

1. Round bottomed microtitre plates (e.g. Falcon 3910).

2. Washing medium: 0.1% bovine serum albumin (BSA) in phosphate buffered saline (PBS) containing 0.05% sodium azide.

3. Normal human serum (heat inactivated at 56° C. for 30 min).

4. CAMPATH-1H antibody (clinical grade) at a known concentration.

5. FITC-labelled anti-(human IgG1) (e.g. Sigma F0767). The use of a monoclonal, isotype specific detection reagent is strongly recommended. The optimum titre should be determined by trial experiments with standard samples of CAMPATH-1H diluted in normal human serum.

6. Culture of transfectant cell line (e.g. BHK-CAM-G1, baby hamster kidney cells as described in Example 1). This should be maintained in exponential growth in selective culture medium (e.g. Iscove's modified Dulbecco's medium, IMDM containing 5% foetal calf serum (FCS) and 2 mg/ml G418). About 20 ml of culture will be required for each microtitre plate.

(iii) Method

1. Prepare a set of standards containing (e.g.) 0, 0.1, 0.2, 0.5, 1.0, 2.0, 5.0, 10.0 µg/ml CAMPATH-1H diluted in heat-inactivated normal human serum.

2. Incubate the test sera at 56° C. for 30 min to inactivate complement.

3. Pipette 50 µl of test and standard sera into the wells of a microtitre plate according to a predetermined plan.

4. Harvest the cells by centrifugation at 1000 rpm for 10 min. Discard the culture supernatant and resuspend the cells in approx 25% of their original volume of washing medium. The cell density should be approx $1-2 \times 10^6$ per ml. Adjust it if necessary.

5. Add 50 µl of cell suspension to each well. Incubate on ice for 30 min.

6. Add washing medium to give a final volume of 200 µl and resuspend the cells. Centrifuge the plate at 1000 rpm for 1 min and aspirate off the supernatants. Avoid cross-contamination.

7. Repeat step 6 another four times.

8. Resuspend the cell in 50 µl of FITC-labelled anti-(human IgG1) diluted in washing medium to the optimal titre. Incubate on ice for 30 min.

9. Repeat step 6 three times.

10. Resuspend the cells in 100 µl of washing medium. Add 50 µl of 3% formaldehyde and mix. Store at 4° C. until required for analysis.

11. Analyse by flow cytometry. Gate the cells according to forward and 90° scatter and record the mean fluorescence of all cells falling within the gate.

12. Plot a graph of mean fluorescence versus antibody concentration for the standard samples and calculate the concentration of antibody in the test samples by interpolation. Results are only valid for sub-saturating concentrations of antibody (usually less than 5 µg/ml) and it may be necessary to dilute the test samples if higher concentrations are encountered.

(iv) Variations

There are numerous possible variations to this assay which may be useful in various circumstances. Some examples are given below:

1. Alternative CDw52 positive transfectants could be used. It is desirable that they should exhibit intense staining with a positive control and very weak staining with normal human serum alone. The ultimate sensitivity of the assay depends on the ratio between these two results.

2. An alternative washing medium could be used, e.g. HEPES-buffered tissue culture medium, or balanced salts solutions. It is desirable to add a source of protein, e.g. BSA or FCS to reduce non-specific binding and sodium azide as preservative and to prevent patching or capping of antigen during the experiment.

3. The assay can equally well be used to detect other anti-CDw52 antibodies, either human or rat. A suitable detection reagent would be required. Usually this assay is more sensitive for detection of rat CDw52 antibodies (e.g. CAMPATH-1G) because interference from normal human IgG in the serum is negligible.

4. The assay could be carried out in suitable tubes as well as microtitre plates. Possibly the number of wash cycles at step 7 could then be reduced.

5. Inactivation of complement can be accomplished by adding EDTA to a final concentration of 5 mM to the washing medium instead of heat inactivation of the serum samples.

EXAMPLE 5

Measurement of Blocking Substances in Serum Samples (i) Rationale

In principle, the binding of anti-CDw52 antibodies to cells might be blocked by the presence, in patient's sera, or either free antigen or antibodies directed against the anti-CDw52 antibody. Such blocking substances can be detected by the inhibition of binding of a fixed amount of CDw52 antibody to a transfected cell line expressing the CDw52 antigen cDNA. Binding is measured by indirect immunofluorescence in the same way as for measurement of anti-CDw52 antibodies in serum samples. This assay is not appropriate for samples taken during antibody therapy when anti-CDw52 antibodies in the serum could interfere.

(ii) Materials

1. Round bottomed microtitre plates (e.g. Falcon 3910).

2. Washing medium: 0.1% bovine serum albumin (BSA) in phosphate buffered saline (PBS) containing 0.05% sodium azide.

3. Normal human serum (heat inactivated at 56° C. for 30 min).

4. CAMPATH-1H antibody (clinical grade) at a known concentration.

5. FITC-labelled anti-(human IgG1) (e.g. Sigma F0767). The use of a monoclonal, isotype specific detection reagent is strongly recommended. The optimum titre should be determined by trial experiments with standard samples of CAMPATH-1H diluted in normal human serum.

6. Culture of transfectant cell line (e.g. BHK-CAM-G1, baby hamster kidney cells as described in Example 1). This should be maintained in exponential growth in selective culture medium (e.g. Iscove's modified Dulbecco's medium, IMDM) containing 5% foetal calf serum (FCS) and 2 mg/ml G418. About 20 ml of culture will be required for each microtitre plate.

7. Standard samples of blocking substances, e.g. monoclonal anti-idiotype antibody (e.g. YID13.9), high-titre polyclonal anti-idiotype antibodies from patients who received multiple courses of treatment (e.g. Col) and/or purified CDw52 antigen from human spleen. The titre of these standards should be established by trial experiments.

(iii) Method

1. Prepare two sets of standards, one containing (e.g.) 0, 0.1, 0.2, 0.5, 1.0, 2.0, 5.0, 10.0 µg/ml CAMPATH-1H diluted in heat-inactivated normal human serum, and the other containing various dilutions of standard blocking substances diluted in heat-inactivated normal human serum according to the predetermined titres.

2. Incubate the test sera at 50° C. for 30 min to inactivate complement.

3. Pipette 25 µl of a test and standard sera (in duplicate) into the wells of a microtitre plate according to a predetermined plan. Control sera taken from the patient before antibody therapy as well as normal human serum should also be included.

3a. Add 25 µl of CAMPATH-1H diluted to 1 or 5 µg/ml in washing medium to each sample. Add 25 µl of washing medium alone to the samples containing CAMPATH-1H standards. Incubate on ice for 30 min.

4. Harvest the cells by centrifugation at 1000 rpm for 10 min. Discard the culture supernatant and resuspend the cells in approx 25% of their original volume of washing medium. The cell density should be approx $1-2 \times 10^6$ per ml. Adjust it if necessary.

5. Add 50 μl of cell resuspension to each well. Incubate on ice for 30 min.

6. Add washing medium to give a final volume of 200 μl and resuspend the cells. Centrifuge the plate at 1000 rpm for 1 min and aspirate off the supernatants. Avoid cross-contamination.

7. Repeat step 6 another four times.

8. Resuspend the cell in 50 μl of FITC-labelled anti-(human IgG1) diluted in washing medium to the optimal titre. Incubate on ice for 30 min.

9. Repeat step 6 three times.

10. Resuspend the cells in 100 μl of washing medium. Add 50 μl of 3% formaldehyde and mix. Store at 4° C. until required for analysis.

11. Analyse by flow cytometry. Gate the cells according to forward and 90° scatter and record the mean fluorescence of all cells falling within the gate.

12. Plot a graph of mean fluorescence versus antibody concentration for the standard samples and calculate the concentration of available antibody in the other samples by interpolation. The molar concentration of blocking substance is then at least equivalent to the amount of antibody inhibited from binding to the target cells. (It could be significantly higher if the affinity of interaction is low.) Results can only be quantified when inhibition of binding between about 20% and 80%. The assay is therefore carried out at two levels of CAMPATH-1H to allow for a wider range of sensitivity. However, it may be necessary to dilute the test samples if high concentrations of blocking substance are encountered.

(iv) Variations

Similar variations to this assay could be introduced as in the assay for serum levels of anti-CDw52 antibodies.

EXAMPLE 6

Extraction and Purification of CDw52 Antigen $2.66 \times 10^7$ CHO cells expressing CDw52 antigen (Example 2) grown in 10% FBS plus methotrexate were centrifuged (9K, 5 minutes, 4° C.) and washed once with PBS. The cells were extracted with chloroform:methanol:water (4:8:3; 5ml) with vortexing (5 minutes), left to stand for 15 minutes, centrifuged (9K, 10 minutes, 4° C.) and the supernatant was collected. The extraction was repeated and the supernatants bulked to provide a total volume of 10 ml. 1.73ml of water was added to give a ratio of chloroform:methanol:water of 4:8:5.6. The mixture was centrifuged (9K, 10 minutes, 4° C.), and the upper phase was collected and evaporated to dryness on a rotary evaporator. The upper phase was dialysed against water (4×2 liters; 4° C.; 48 hours) and stored at 4° C. in water plus 0.02% azide (3.07ml).

The upper phase (3.07ml) was diluted with 10×Buffer A (5% propanol, 0.01M ammonium acetate). A 20 μl aliquot was taken, diluted further to 500 μl, and shown by an ELISA assay to contain CDw52 antigen. Comparison with a standard preparation containing 500 mU/ml CDw52 antigen showed that the 3.07ml of upper phase contained 160 mU/ml CDw52 antigen.

The remainder of the diluted upper phase was subjected to Octyl Sepharose chromatography on an HR 5/20 column (0.5×20 cm; Pharmacia) eluted with 50% propanol (25 ml), precycled with a linear gradient of Buffer A to 60% propanol and then reequilibrated with Buffer A. The flow rate was 4.6 ml/hour. The diluted upper phase was applied to the Octyl Sepharose column at a rate of 2 ml/hour and eluted with 5 ml Buffer A (unbound fraction). The column was then eluted with a gradient of Buffer A to 60% propanol (total 100 ml) at a flow rate of 4.6 ml/hour. 100 fractions of about 1 ml each (duration of collection of each fraction about 13 minutes) were collected and each fraction was analysed for CDw52 antigen content by ELISA. Virtually all of the CDw52 antigen was found to be present in fractions 40 to 56. A main peak at about fraction 46 (about 90%) indicated CDw52 antigen present in PILPC-sensitive form and a second peak at about fraction 52 (10%) suggested a PIPLC-resistant form.

We claim:

1. A recombinant eukaryotic, non-human cell line capable of expressing recombinant CDw52 antigen or an antigenic fragment thereof in a form capable of being recognized by antibodies raised against the human CDw52 antigen, wherein said cell line is a CHO or BHK cell line.

2. The cell line according to claim 1 wherein said cell line is said CHO cell line.

3. The cell line according to claim 1 wherein said cell line is said BHK cell line.

4. A method for the production of recombinant CDw52 antigen or an antigenic fragment thereof which comprises the steps of:

(i) providing a suitable eukaryotic, non-human host cell line capable of processing CDw52 antigen or an antigenic fragment thereof into a form recognized by antibodies raised against natural human CDw52 antigen and transformed with DNA encoding the CDw52 antigen or an antigenic fragment thereof in a form capable of expression;

(ii) growing cell line in a manner such that the CDw52 antigen or the antigenic fragment thereof is expressed in a form recognized by antibodies raised against natural human CDw52 antigen; and (iii) recovering the recombinant CDw52 antigen or the antigenic fragment thereof, wherein the cell line is a CHO or BHK cell line.

5. The method according to claim 4 wherein said cell line is said CHO cell line.

6. The method according to claim 4 wherein said cell line is said BHK cell line.

* * * * *